US009314014B2

(12) United States Patent
Hess et al.

(10) Patent No.: US 9,314,014 B2
(45) Date of Patent: *Apr. 19, 2016

(54) COMPOSITIONS AND METHODS FOR THE STORAGE OF RED BLOOD CELLS

(75) Inventors: John R. Hess, Bethesda, MD (US); Tibor J. Greenwalt, Cincinnati, OH (US)

(73) Assignees: University of Maryland, Baltimore, Baltimore, MD (US); University of Cincinnati, Cincinnati, OH (US)

( * ) Notice: Subject to any disclaimer, the term of this patent is extended or adjusted under 35 U.S.C. 154(b) by 1005 days.

This patent is subject to a terminal disclaimer.

(21) Appl. No.: 11/060,026

(22) Filed: Feb. 17, 2005

(65) Prior Publication Data

US 2005/0233302 A1    Oct. 20, 2005

Related U.S. Application Data

(60) Provisional application No. 60/545,582, filed on Feb. 18, 2004.

(51) Int. Cl.
*A01N 1/02* (2006.01)
*C12N 5/078* (2010.01)

(52) U.S. Cl.
CPC *A01N 1/021* (2013.01); *A01N 1/02* (2013.01); *A01N 1/0221* (2013.01); *A01N 1/0226* (2013.01); *C12N 5/0641* (2013.01)

(58) Field of Classification Search
CPC .. A61K 35/18; A61K 2035/124; A01N 1/021
See application file for complete search history.

(56) References Cited

U.S. PATENT DOCUMENTS

| | | | |
|---|---|---|---|
| 4,267,269 A | 5/1981 | Grode et al. | 435/2 |
| 4,585,735 A | 4/1986 | Meryman et al. | 435/2 |
| 4,675,185 A | 6/1987 | Kandler et al. | 424/101 |
| 5,248,506 A * | 9/1993 | Holme et al. | 424/533 |
| 5,250,303 A | 10/1993 | Meryman | |
| 5,476,764 A | 12/1995 | Bitensky | 435/2 |
| 5,487,971 A | 1/1996 | Holme et al. | 435/2 |
| 5,624,794 A | 4/1997 | Bitensky et al. | 435/2 |
| 5,690,963 A | 11/1997 | Spargo et al. | 424/533 |
| 5,769,839 A | 6/1998 | Carmen et al. | 604/408 |
| 5,789,151 A | 8/1998 | Bitensky et al. | 435/2 |
| 5,906,915 A | 5/1999 | Payrat et al. | 435/2 |
| 6,150,085 A | 11/2000 | Hess et al. | |
| 6,447,987 B1 * | 9/2002 | Hess et al. | 435/2 |
| 6,527,957 B1 | 3/2003 | Deniega et al. | 210/651 |
| 7,723,017 B2 | 5/2010 | Bitensky et al. | 435/2 |
| 2005/0191354 A1 | 9/2005 | Jean et al. | 424/486 |
| 2005/0233302 A1 | 10/2005 | Hess et al. | 435/2 |

FOREIGN PATENT DOCUMENTS

| | | | | |
|---|---|---|---|---|
| CN | 1182349 A | 5/1998 | | A01N 1/02 |
| CN | 1186596 A | 7/1998 | | A01N 1/00 |
| EP | 0 313 808 A2 | 5/1989 | | C12N 5/02 |
| FR | 2 581 289 A1 | 11/1986 | | A01N 1/00 |
| JP | 63-63616 | 3/1988 | | A61K 35/14 |
| JP | 63-146824 | 6/1988 | | A61K 35/14 |
| JP | 02-48522 | 2/1990 | | A61K 31/02 |
| JP | 02-48522 A | 2/1990 | | A61K 31/02 |
| JP | 02-152923 A | 6/1990 | | A61K 31/66 |
| JP | 02-187661 A | 7/1990 | | G01N 33/48 |
| JP | 02-291221 A | 12/1990 | | A01H 4/00 |
| JP | 04-504841 A | 8/1992 | | A61K 35/14 |
| JP | 05-503075 A | 5/1993 | | A01N 1/02 |
| JP | 05-503304 A | 6/1993 | | A01N 1/00 |
| JP | 06-135851 A | 5/1994 | | A61K 37/54 |
| JP | 09-20687 A | 1/1997 | | A61K 45/00 |
| JP | 2000-516963 A | 12/2000 | | A61K 35/18 |
| JP | 2004-503336 A | 2/2004 | | A61M 5/142 |
| JP | 2004-523521 A | 8/2004 | | A61K 45/06 |
| WO | WO 81/02239 A1 | 8/1981 | | A01N 1/02 |
| WO | WO 89/02274 A1 | 3/1989 | | A61K 35/18 |
| WO | WO 91/04659 A1 | 4/1991 | | A01N 1/02 |
| WO | WO 92/08348 | 5/1992 | | |
| WO | WO 92/08348 A1 | 5/1992 | | A01N 1/00 |
| WO | WO 92/08349 A1 | 5/1992 | | A01N 1/02 |
| WO | WO 96/29863 A1 | 10/1996 | | A01N 1/02 |
| WO | WO 98/51147 | 11/1998 | | |
| WO | WO 00/11946 A2 | 3/2000 | | |
| WO | WO 02/05873 A2 | 1/2002 | | |

(Continued)

OTHER PUBLICATIONS

Grant & Hackh's Chemical Dictionary, Fifth Edition, eds. Grant and Grant, McGraw-Hill Book Co., 1987, p. 559, definition of "sugar".*
Hess et al., "Twelve-week RBC Storage", Transfusion 43 : 867 (2003).*
Woods et al., "The Effect of Periodic Mixing on the Preservation of 2,3-Diphosphoglycerate (2,3-DPG) Levels in Stored Blood", Blood 42 (1) :17-25 (1973).*
Grant & Hackh's Chemical Dictionary, Fifth Edition, McGraw-Hill Bood Company, definition of "glucose", pp. 263-264 (1987).*
Bensigner et al., "Prolonged maintenance of 2,3-DPG in liquid blood storage: Use of an internal CO2 trap to stabilize pH", J. Laboratory and Clinical Medicine 89: 498-503 (1977).*
Beutler, M.D., et al., Preservation of red cell 2,3-DPG [diphosphoglycerate] and viability in bicarbonate containing medium, Journal of Laboratory and Clinical Medicine, (1972), vol. 80, pp. 723-728, Abstract Only.
Bensinger, A., et al. Prolonged Maintenance of 2-3-di-phosphoglyerate in Liquid Blood Storage; Use of an Internal Carbon Dioxide trap to Stabilize PH; Journal of Laboratory and Clinical Medicine; vol. 89, No. 3; pp. 498-503, Abstract Only.

(Continued)

*Primary Examiner* — Renee Claytor
*Assistant Examiner* — Susan E Fernandez
(74) *Attorney, Agent, or Firm* — Sunstein Kann Murphy & Timbers LLP

(57) ABSTRACT

The present invention provides an aqueous composition for storage of red blood cells consisting essentially of: adenine; dextrose; at least one non-metabolizable membrane-protectant sugar; and a specifically defined pH buffering system. Also provided are improved methods for preserving red blood cells and methods for increasing the viability, membrane retention, and recoverability while suppressing apoptosis, hemolysis, and post-reinfusion clearance of stored red blood cells which utilize the novel compositions.

39 Claims, 2 Drawing Sheets

(56) References Cited

FOREIGN PATENT DOCUMENTS

| WO | WO 02/23988 A1 | 3/2002 | ............... A01N 1/02 |
| WO | WO 03/043419 | 5/2003 | |

OTHER PUBLICATIONS

Hess et al., "Twelve-week RBC storage," *Transfusion*, vol. 43, No. 7, pp. 867-872 (Jul. 2003).
Hess et al., "The role of electrolytes and pH in RBC ASs," *Transfusion*, vol. 41, No. 8, pp. 1045-1051 (Aug. 2001).
Hess et al., "RBC storage for 11 weeks," *Transfusion*, vol. 41, No. 12, pp. 1586-1590 (Dec. 2001).
Australian Intellectual Property Office, Examiner's First Report—Application No. 2005327576, dated Aug. 11, 2010 (2 pages).
Australian Intellectual Property Office, Examiner's Report No. 2—Application No. 2005327576, dated Jun. 22, 2011 (2 pages).
Canadian Intellectual Property Office, Official Action—Application No. 2,598,366, dated Jan. 17, 2013 (3 pages).
The Eurasion Patent Office, Official Action—Application No. 200701660, dated Feb. 3, 2010 (2 pages).
The Eurasion Patent Office, Official Action—Application No. 200701660, dated Dec. 3, 2010 (3 pages).
The Eurasion Patent Office, Official Action—Application No. 200701660, dated Aug. 29, 2011 (3 pages).
The Eurasion Patent Office, Official Action—Application No. 200701660, dated Aug. 29, 2011 (4 pages).
The Eurasion Patent Office, Official Action—Application No. 200701660, dated Sep. 12, 2013 (2 pages).
Japanese Patent Office, Official Action—Application No. 2012-034275, dated Oct. 10, 2013 (7 pages).
Japanese Patent Office, Official Action (Notice for Reasons of Rejection)—Application No. 2012-034275, dated Oct. 10, 2013 (7 pages).
American Association of Blood Banks, *Technical Manual*, p. 52 (1993).
Beutler et al., "Volume control of erythrocytes during storage," *Transfus.*, vol. 28, No. 4, pp. 353-357 (Jul.-Aug. 1988).
Beutler E., "Back to the future in RBC preservation," *Transfus.*, vol. 40, pp. 893-895 (Jan. 2000).
Dumaswala et al., "Studies in red blood cell preservation: 9. The role of glutamine in red cell preservation," *Vox Sang.*, vol. 67, No. 3, pp. 255-259 (Oct. 1994).
Dumaswala et al., "Improved red blood cell preservation correlates with decreased loss of bands 3, 4.1, acetylcholinestrase, and lipids in microvesicles," *Blood*, vol. 87, No. 4, pp. 1612-1616 (1996).
Dumaswala et al., "Glutamine- and Phosphate-Containing Hypotonic Storage Media Better Maintain Erythrocyte Membrane Physical Properties," Blood, vol. 88, No. pp. 697-704 (Jul. 1996).
Greenwalt et al., "Studies in red blood cell preservation 10. $^{51}$Cr recovery of red cells after liquid storage in a glycerol-containing additive solution," *Vox Sang.*, vol. 70, No. 1, pp. 6-10 (Jan. 1996).
Greenwalt et al., "The effect of hypotonicity, glutamine, and glycine on red cell preservation," *Trans.*, vol. 37, No. 3, pp. 269-276 (1997).
Hess et al., "Extended Liquid Storage of Red Blood Cells," *Forum on Blood Safety and Blood Availability, Division of Health Sciences Policy, Institute of Medicine*, pp. 99-102 (1996).
Hess et al., "Alkaline CPD and the preservation of RBC, 2,3-DPG," *Tranfus.*, vol. 42, No. 6, pp. 747-752 (Jun. 2002).
Hess et al., "Buffering and dilution in red blood cell storage," *Tranfus.*, vol. 42, pp. 50-54 (2006).
Högman et al., "Half-strength citrate CPD and new additive solutions for improved blood preservation. I. Studies of six experimental solutions," *Transfus. Med.*, vol. No. 1, pp. 43-50 (Mar. 1993).
Högman et al., "Shall red cell units stand upright, lie flat or be mixed during storage? In vitro studies of red cells collected in 0.5 CPD and stored in RAS2 (Erythrosol.RTM)," *Tranfus. Sci.*, vol. 16, No. 2, pp. 193-199 (Jun. 1995).
Mazor et al., "Prolonged Storage of Red Cells: The Effect of pH, Adenine and Phosphate," *Vox Sang.*, vol. 66, No. 4, pp. 264-269 (1994).
Meryman et al., "Prolonged storage of red cells at 4° C," *Transf.*, vol. 26, No. 6, pp. 500-505 (Nov.-Dec. 1986).
Meryman et al., "Extending the storage of red cells at 4° C," *Transf. Sci.*, vol. 15, No. 2, pp. 105-115 (Jun. 1994).
Moore et al., "Liquid storage at 4° C of previously frozen red cells," *Transfus.*, vol. 27, No. 6, pp. 496-498 (Nov.-Dec. 1987).
Ohkuma et al., "The preservative-exchange method using a sextuple-bag system for a 10-week storage period of red blood cells," *Tranfus. Med.*, vol. 1, No. 4, pp. 257-262 (Dec. 1991).
European Patent Office W. Muellners, Authorized officer, European Search Report—Application No. 11008822.6-2103, dated Jan. 23, 2012 (11 pages).
European Patent Office G. Marie, Communication pursuant to Application No. 11 008 822.6-2103, dated Jan. 14, 2013 (6 pages).
European Patent Office W. Muellners, Authorized officer, International Search Report—Application No. PCT/US2000/025712, dated Jul. 31, 2001 (4 pages).
European Patent Office R. Faizi, Authorized officer, International Search Report—Application No. PCT/US1999/019946, dated Jun. 29, 2000 (3 pages).
European Patent Office G. Marie, Authorized officer, International Search Report—Application No. PCT/US2005/005004, dated Feb. 13, 2006 (5 pages).
European Patent Office G. Marie, Authorized officer, International Preliminary Report on Patentability—Application No. PCT/US2005/005004, dated Aug. 21, 2007 (8 pages).
Communication pursuant to Article 94(3) EPC, Application No. 05 810 134.6-2103, dated Nov. 6, 2009 (6 pages).
European Patent Office G. Marie, Communication Pursuant to Article 94(3) EPC, Application No. 05 810 134.6-2103, dated Jan. 14, 2013 (7 pages).
Appeal Board Japanese Patent Office, Decision on Appeal—Appeal No. 2012-3237, dated Mar. 11, 2014 (23 pages).
Appeal Board Japanese Patent Office, Decision on Appeal—Appeal No. 2012-3237, dated Mar. 11, 2014 (21 pages).
Canadian Intellectual Property Office, Official Action—Application No. 2,598,366, dated Mar. 12, 2012 (3 pages).
State Intellectual Property Office of People's Republic of China, Official Action—Application No. 200580049506.0, May 17, 2010 (7 pages).
State Intellectual Property Office of People's Republic of China, First Office Action—Application No. 200580049506.0, May 17, 2010 (11 pages).
State Intellectual Property Office of People's Republic of China, Notice of Reexamination—Application No. 200580049506.0, dated Apr. 20, 2012 (6 pages).
State Intellectual Property Office of People's Republic of China, Notice of Reexamination—Application No. 200580049506.0, dated Apr. 20, 2012 (8 pages).
State Intellectual Property Office of People's Republic of China, Search Report—Application No. 201310069111.3 (3 pages).
European Patent Office, Written Opinion of the International Searching Authority—Application No. PCT/US2005/005004, dated Aug. 17, 2007 (7 pages).
Japanese Patent Office, Notice of Reasons for Rejection—Application No. 2007-556120, dated Nov. 17, 2010 (7 pages).
Japanese Patent Office, Decision of Rejection—Application No. 2007-556120, dated Oct. 6, 2011 (3 pages).
Hess et al., "Storage of red blood cells: New approaches," *Transf.*, vol. 16, No. 4, pp. 283-295 (Oct. 2002).
Canadian Patent Office, Notice of Allowance—Application No. 2,598,366, dated Sep. 23, 2013 (1 page).
State Intellectual Property Office of People's Republic of China, Official Communication—Application No. 200580049506.0, dated Feb. 18, 2011 (6 pages).
State Intellectual Property Office of People's Republic of China, Official Communication (Decision on Rejection)—Application No. 200580049506.0, dated Feb. 18, 2011 (8 pages).
Eurasian Patent Office, Official Action—Application No. 200701660, dated Mar. 28, 2014 (3 pages).

(56) References Cited

OTHER PUBLICATIONS

Eurasian Patent Office, Official Action (Notification of the Need to Submit Additional Materials)—Application No. 200701660, dated Mar. 28, 2014 (4 pages).

Soumen Ghosh, Asst. Controller of Patents & Designs Government of India Patent Office, First Examination Report—Application No. 3149/KOLNP/2007, dated Oct. 28, 2013 (2 pages).

Japanese Patent Office, Decision of Patent—Application No. 2012-034275, dated Jun. 17, 2014 (1 page).

Japanese Patent Office, Transcript of Decision of Patent—Application No. 2012-034275, dated Jun. 17, 2014 (1 page).

Hess et al., "Twelve-week RBS storage", Transfusion, vol. 43, No. 7, pp. 867-872 (Jun. 2003).

Hitoshi Ito, Commissioner of the Japan Patent Office, First Brief of Defendant, Suit Case No. H26 (g-ke) 10165 dated Oct. 15, 2014.

State Intellectual Property Office, P.R., China Second Office Action, Application No. 201310069111.3 dated Sep. 26, 2014.

Wood et al., "The Viability of Human Blood Stored in Phosphate Adenine Media", Transfusion, vol. 7, No. 6 (Nov-Dec. 1967).

Wood et al., "Storage of Erythrocytes in Artificial Media", Transfusion, vol. 11, pp. 123-133 (1971).

\* cited by examiner

COMPOSITIONS AND METHODS FOR THE STORAGE OF RED BLOOD CELLS

CROSS-REFERENCE TO RELATED APPLICATIONS

This application claims priority based on U.S. provisional application No. 60/545,582, filed on Feb. 18, 2004.

STATEMENT REGARDING FEDERALLY SPONSORED RESEARCH OR DEVELOPMENT

Portions of this work were performed under U.S. Army contract DAMD 17-95-C-5029 and the U.S. government may have an ownership interest herein.

BACKGROUND OF THE INVENTION

The invention generally relates to compositions and methods associated with the storage of red blood cells (RBCs). In particular, it relates to an improved RBC storage composition and processes and applications thereof.

The ability to store and preserve red blood cells (RBCs) for later re-infusion into patients is a relatively recent technological development that was the harbinger to modern surgical practice. Such preservation is scientifically tricky and the steps to achieving longer storage duration and higher quality re-infused red blood cells have been incremental. As soon as they are collected from a donor, red blood cells begin to die as they coagulate, starve, lose ATP, 2,3-DPG, membrane surface area and integrity, and hemoglobin (Hb). Rous & Turner in 1916 and Robertson in 1917 first demonstrated successful whole blood storage. Acid-citrate-dextrose (ACD, 1943), comprising citrate as an anti-coagulant and dextrose as the sole nutrient utilized by red blood cells, and Citrate-phosphate-dextrose solution (CPD, 1957), adding phosphate as a metabolic source and for membrane retention, were subsequently approved for 21-day storage of whole blood. CPD with adenine (CPDA-1, 1979) was later introduced and used for extending the shelf life of stored whole blood and packed RBCs for up to 5 weeks.

Initially, storage compositions were designed to be acidic to prevent the caramelization of the glucose during the heat sterilization performed in the final production step. In the 1950s, adenine was discovered to be useful as an additive and replaces the adenine lost by deamination. In the 1970s it became desirable to remove the plasma from the collected whole blood for platelets and for the manufacture of plasma derivatives. This, however, led to a reduction in the percent recovery of the resulting "packed RBC."

To circumvent this, compositions known in the art as additive solutions (AS) were developed to restore volume, nutrients, and other useful RBC stabilizers. Additive solution compositions for the preservation of red blood cells (RBCs) after their separation from whole blood are intended to be tailored specifically to the needs of RBCs. The development of certain additive solutions extended RBC storage to 6 weeks in 1981. Red blood cells (RBCs) stored in these solutions, however, undergo steady deterioration after about 6 weeks as determined by the inability of 75% of such cells to survive in the circulation for 24 hours after re-infusion back into the human donor. It has been observed that during continued refrigerated storage, glucose is consumed at a decreasing rate, as the concentration of metabolic waste, i.e. lactic acid and hydrogen ions, increases. Such a decrease in the rate of glucose metabolism leads to depletion of adenosine triphosphate (ATP), which directly correlates to the recovery of RBCs when the cells are returned to the circulation. Additive solutions such as Adsol® (AS-1), Nutricel® (AS-3), Optisol® (AS-5), and ErythroSol® were designed to extend the storage of RBCs at 1-6° C. All three ASs currently licensed in the U.S., AS-1, AS-3, and AS-5, contain saline, adenine, glucose and some citrate and/or mannitol as "membrane protectants." AS-3 also contains monosodium phosphate. Each of the U.S.-licensed ASs meet the licensure requirements for 6-week RBC storage, but fail to achieve 7-week storage. Presently licensed RBC additive solution compositions were developed before the RBC storage lesion (defined herein as the sum of the survival- and/or function-limiting effects of storage on RBCs) was understood to be an apoptotic process.

Almost all of the whole blood collected now is made into components, and the RBC fraction is stored as packed RBCs. For blood drawn into the additive solution systems, RBCs are packed by centrifugation, plasma is removed so that RBCs make up 80% of the volume, and then 100 ml of additive solution is added sterilely. The resulting suspensions have a RBC volume fraction of approximately 55%. RBCs stored in the conventional FDA-approved additive solutions can be stored for only 6 weeks with an acceptable 24-hour in vivo recovery.

To increase the time of acceptable in vivo recovery of RBCs re-infused into patients after a storage period, attempts have been made to improve the additive solutions and storage processes. In "Studies In Red Blood Cell Preservation-7. In vivo and in vitro Studies With A Modified Phosphate-Ammonium Additive Solution," by Greenwalt et al., Vox. Sang. 65:87-94 (1993), the authors determined that an experimental additive solution (designated EAS-2) containing (in mM): 20 $NH_4Cl$, 30 $Na_2 HPO_4$, 2 adenine, 110 dextrose, 55 mannitol, formulated at a pH of 7.15, is useful in extending the storage shelf-life of human RBCs from the current standard of 5-6 weeks to an improved standard of 8-9 weeks. However, packed RBCs stored in EAS-2 were not directly infusible but required the removal of the supernatant with a washing step prior to transfusion due to the presence of ammonium in the additive solution.

In "Studies in Red Blood Cell Preservation-8; Liquid Storage of Red Cells in Glycerol-Containing Additive Solution," Vox. Sang. 67:139-143 (1994), Greenwalt et al. described an additive solution (designated EAS-25) that allowed 73 percent recovery of packed red cells after nine weeks. However, the resulting RBC units contained about 1 percent glycerol and thus, are not safe for transfusion in humans in large amounts.

In "Extending the Storage of Red Cells at 4.degree. C.," Transfus. Sci. 15:105-115 (1994) by Meryman et al., acceptable viability of RBCs stored in very dilute suspensions at low hematocrit for as long as 27 weeks were demonstrated. However, such stored RBC suspensions were not acceptable for direct infusion due to their high content of potassium and ammonia and their low volume fraction of RBCs. The 5 L of solution for 200 mL of RBC required to produce his observed beneficial effects were not clinically practicable.

With respect to approved and commercially available products, the additive solutions presently licensed in the U.S. work for only about 6 weeks with an average recovery of about 80%. Two additive solutions presently licensed in Europe work for about 7 weeks with an average recoveries of 77% (ErythroSol from Baxter Healthcare, La Chatre, France) and 75% (PAGGS mannitol from Maco Pharma). Novel solutions recently described by Kurup et al. (Vox Sang 2003: 85:253-261) may be expected to have shorter storage times because of the lower ATP concentrations.

In response to the deficiencies in these prior findings, the present inventors developed lower volume disodium phosphate-containing alkaline experimental additive solutions (EASs) that partially neutralize the effect of collecting blood into acidic anticoagulant solutions such as CPD (citrate-phosphate-dextrose), and showed that these EASs improved RBC ATP concentrations, reduced hemolysis, and appeared to decrease RBC membrane morphological changes and loss (see U.S. Pat. Nos. 6,150,085 and 6,447,987 to Hess and Greenwalt, the complete disclosures of which are fully incorporated herein by reference). Various EASs were shown to support between 9 and 12 weeks of storage. Although these EASs yielded superior performance results, they contained sodium chloride and were formulated to require a relatively large volume resulting in greater dilution of the stored RBC, thus increasing the risk of hemodilution in multiply transfused patient recipients. In addition, the presence of sodium chloride created a solubility limit on the amount of buffering salts and phosphates that the system could sustain at desirable volumes.

Increased duration of RBC storage remains an important consideration during periods when demand is high but intermittent, such as during wartime, and for geographical regions that require transfusable blood but only on an inconsistent and sporadic basis. In fact, given the current level of reported waste due to expiration of the safe storage period prior to realization of a demand in general, increasing the duration of time that RBCs may be safely stored is an ongoing ubiquitous concern.

Thus, there is a need for RBC storage compositions formulated to retain or enhance recovery and performance benefits in the lower volumes of conventional additive solutions. There is a continuing need in the blood storage and transfusion art for improved RBC storage that results in longer storage duration, better recovery percentage, and improved physiological functioning of the transfused RBC. Consequently, there remains a need for improved RBC storage compositions and processes of manufacture thereof. There is also a continuing need for additive compositions which allow the RBC suspension to which the composition is added to be directly infused into humans, and which permit an acceptable post-infusion recoverability of viable RBCs possessing enhanced physiological functioning capabilities and lower rates of clearance from the infused patient's circulation.

SUMMARY OF THE INVENTION

Accordingly, the present invention provides novel compositions suitable for the storage and preservation of collected red blood cells. The present inventors surprisingly discovered that substantially eliminating sodium chloride from such compositions, previously considered to be essential to proper operation of storage compositions, provides an increased capacity in the composition for an enhanced pH buffering system which, in turn, provides benefits both in terms of the integrity and physiological functioning quality of the stored and then re-infused red blood cells, and with respect to the length of time the RBCs may be stored with retention of the recoverability and hemolysis levels required under regulatory law for licensing. In addition, the inventive compositions retain their superior performance at conventional volumes, making them particularly suitable for storing red blood cells which may be targeted for infusion into multiply or massively transfused patients.

One embodiment of the present invention provides a composition for storage of red blood cells at about 1 to about 6° C. The composition consists essentially of: adenine; dextrose; at least one nonmetabolizable membrane-protectant sugar; and a pH buffering system. The pH buffering system comprises sodium bicarbonate and disodium phosphate and is present in an amount sufficient for the composition to have a pH of from about 8 to about 9. The composition is operable to maintain a pH of a red blood cell (RBC) suspension to which the composition is added at a value sufficient to establish and maintain during a storage period a reaction equilibrium in the red blood cell that favors glycolysis over synthesis of 2,3-diphosphoglycerate (DPG) from 1,3-DPG, thereby generating a net gain in adenosine tri phosphate (ATP) with respect to the reaction equilibrium during the storage period. Another embodiment of the invention provides that the composition is substantially free of sodium chloride.

More specific embodiments of the inventive composition are directed to particular components and amounts thereof, and ranges for the osmolarity and pH of the compositions. Other specific embodiments are directed to inventive compositions that are operable to maintain the pH of the red blood cell within particular value ranges.

A further embodiment of the invention is directed to a suspension of red blood cells comprising the inventive composition.

Method embodiments are also provided. One such embodiment is direct to a method of preserving red blood cells (RBCs) for a storage period. The method comprise: (a) mixing a sample of collected whole blood containing the RBCs to be stored and plasma with an anticoagulant solution, thereby forming a suspension of collected whole blood; (b) treating the suspension of collected whole blood to deplete the plasma and concentrate the RBCs, thereby forming packed RBCs; (c) mixing the packed RBCs with an amount of a composition sufficient to form a suspension of RBCs having about 35% to about 70% RBCs by volume; (d) cooling the suspension of RBCs to about 1 to about 6° C.; and (e) storing the cooled suspension of RBCs according to standard bank procedures. The composition consists essentially of: adenine; dextrose; at least one nonmetabolizable membrane-protectant sugar; and a pH buffering system. The pH buffering system comprises sodium bicarbonate and disodium phosphate and is present in an amount sufficient for the composition to have a pH of from about 8 to about 9. The composition is operable to maintain a pH of a red blood cell (RBC) suspension to which the composition is added at a value sufficient to establish and maintain during a storage period a reaction equilibrium in the red blood cell that favors glycolysis over synthesis of 2,3-diphosphoglycerate (DPG) from 1,3-DPG, thereby generating a net gain in adenosine tri phosphate (ATP) with respect to the reaction equilibrium during the storage period. More specific embodiments are also provided.

Additional embodiments are provided which are directed to methods of using the inventive compositions to improve red blood cell (RBC) membrane maintenance and suppress RBC apoptosis during a storage period, to decrease red blood cell (RBC) fragility and suppress RBC hemolysis during a storage period, and to increase viability of red blood cells (RBCs) subsequent to a storage period and after infusion into a patient in need of such an infusion, and decrease a rate of post-infusion clearance of the RBCs by the patient.

Compositions and RBC suspensions produced in accordance with the invention provide a storage period for RBCs throughout which a sufficiently therapeutic amount of the RBCs is recoverable and are directly infusible into patients without further processing in accordance with known standards established and recognized for transfusion of RBCs.

These and additional embodiments and aspects of the present invention will be more fully appreciated by reference to the brief description of the figures, detailed description of the preferred embodiments and examples provided below.

DETAILED DESCRIPTION OF THE PREFERRED EMBODIMENTS

Figure 1:
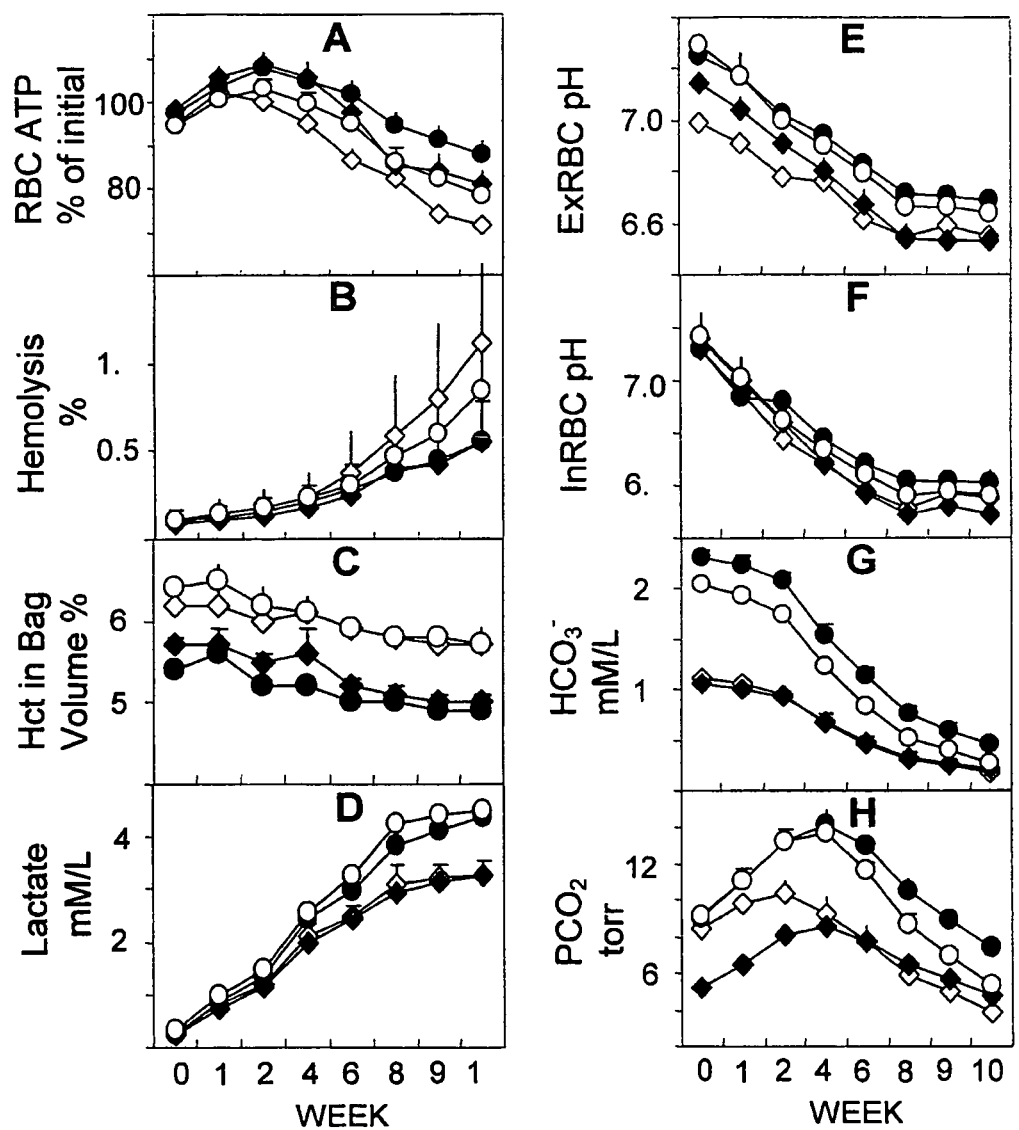
FIG. 1: is a graphical representation of the results of a pooling study showing the effects on RBCs of storage as a function of time in weeks, in 4 different additive solution compositions: 1) AS-3, 110 mL volume (-◇-); EAS-61, 170 mL volume (-◆-); EAS-78, 170 mL, (-●-); and EAS-81, 110 mL, (-○-). Bicarbonate-containing compositions, represented by circles, yield higher ATP concentrations, as illustrated in panel A, than the equivalent volume compositions without bicarbonate, represented by the diamonds. These compositions are also associated with higher lactate concentrations (panel D), higher extracellular and intracellular pH (panels E and F), and higher bicarbonate and $PCO_2$ concentrations (panels G and H). Higher volume compositions, represented by the solid figures, demonstrate reduced hemolysis and reduced storage hematocrit, illustrated in panels B and C, respectively.

The invention generally relates to compositions and methods associated with the storage of red blood cells (RBC). In particular, it relates to novel additive solution compositions and related methods for storage of RBCs that have been separated from whole blood collected in citrate phosphate dextrose (CPD) solution, its variant, citrate phosphate double dextrose (CP2D) solution, or by aphaeresis (removal of whole blood from a patient or donor) in acid citrate dextrose (ACD) or similar solutions.

For purposes of this invention, the term "recovery" is used herein to indicate the fraction of stored RBCs that remains in circulation for 24 hours, after re-infusion into the original human donor.

As used herein, "chloride" refers to anionic chloride. Thus, the term "chloride" includes anionic chloride and the salt forms thereof, such as may be formed from chloride anion(s) and physiologically-acceptable cation(s). The term "chloride" is not intended to include compounds wherein the chloride atom is covalently bonded to, for example, a carbon atom in an organic molecule.

As used herein, the phrase "physiologically-acceptable buffering agent" refers to buffering agents which yield cations and anions either normally found in the blood, plasma, or serum of a human, or that may be tolerated when introduced into a human. Suitable cations include protons, ammonium cations and metal cations. Suitable metal cations include, but are not limited to, the cationic forms of sodium, potassium, calcium, and magnesium, where sodium and potassium are preferred, and sodium is more preferred. An ammonium cation, i.e., a compound of the formula $R4N^+$ where R is hydrogen or an organic group, may be used so long as it is physiologically acceptable. In a preferred embodiment, the cation is selected from hydrogen (i.e., proton), sodium, potassium, calcium, magnesium, and combinations thereof. As used herein, "buffering agent" refers to an agent that adjusts and regulates the pH of a composition.

The inventive compositions disclosed herein are aqueous, that is, they are formulated in water. A preferred water of the invention is treated in order that it is essentially pyrogen-free (i.e., is sterile).

As used herein, "mEq/L" refers to the concentration of a particular component (solute) present in proportion to the amount of water present. More specifically, mEq/L refers to the number of milli-equivalents of solute per liter of water. Milli-equivalents per liter are calculated by multiplying the moles per liter of solute by the number of charged species (groups) per molecule of solute, which is then multiplied by a factor of 1,000.

One embodiment of the present invention provides an aqueous composition for storage of red blood cells at about 1 to about 6° C. The composition consists essentially of: adenine; dextrose; at least one non-metabolizable membrane-protectant sugar; and a pH buffering system. The pH buffering system comprises a combination of physiologically acceptable buffering agents and must include at least one agent that provides bicarbonate anions, at least one agent that provides phosphate anions, and at least one agent that provides sodium cations. The invention contemplates that a single buffering salt may satisfy more than one of these requirements.

It is well known in the red blood cell preservation arts that the concentration of ATP in the red blood cell suspension system is the best correlate of the health of the system. The red blood cell generates ATP through glycolysis via the glycolytic conversion of d-glucose (dextrose) ultimately to lactate. Hence, the concentration curve of lactate is a good indicator of ATP synthesis as well. Regardless of the preservation capacity of the system, red blood cells have a finite life span and the collected red blood cells include a normal distribution of red blood cell ages and proximities to natural death. As no new RBCs are entering the preservation system, there is a limit to the maximum storage period duration that will provide the requisite post-re-infusion recovery percentage. Hence, the ATP-generating capacity of the system as a whole will decrease over time, though; it is typical to see an initial increase upon addition of an additive fluid as it provides nutrients in higher than natural concentrations and the RBC's initially undergo "swelling," which is associated with decreased ATP utilization as well.

Without being bound by theory, it is believed that when stored in additive solution in accordance with the invention, the increased volume of nutrient solution allows an increased mass of substrate to be delivered at acceptable concentrations while providing solute for dilution of metabolic waste products thereby reducing feedback inhibition of glucose metabolism. It is further postulated that another feature of the additive solutions of the invention is that they produce swelling of the RBCs initially followed by a gradual reduction of red cell volume during storage. Such a process has been called "regulated volume decrease." It is hypothesized that during this process either the tyrosine phosphatase activity present in the RBC is suppressed or the tyrosine kinase is activated. Both of these enzymes have been demonstrated to be abundant in the membranes of these cells (Zipser, Y. and Kosower, N. S. (1996) Biochem. J. 314:881; Mallozzi C. et al. (1997) FASEB J. 11: 1281). It is anticipated that the net phosphorylation of the band 3 protein in the RBC membrane would result in the release of phosphofructokinase, aldolase and glyceraldehyde-3-phosphate dehydrogenase in the cytoplasm from their bound state to band 3 (Harrison, M. L. et al. (1991) J. Biol. Chem. 266:4106; Cossins, A. R. and Gibson J. S. (1997) J. Exper. Biol. 200:343; Low, P. S. et al. (1993) J. Biol. Chem. 268:14627; Low, P. S. et al. (1995) Protoplasma 184:1961.

The availability of these three enzymes in the glycolytic pathway would be expected to increase the metabolism of glucose by the RBC, thereby promoting the levels of ATP synthesis and ATP concentration in the RBCs. So, the goal of formulating additive solution compositions is to maintain the ATP synthesis at as high a rate as possible for as long duration as possible.

The present inventors discovered that a key to maximizing the ATP synthesis of the system is to keep the RBC intracellular pH at a level as close to 7.2 as possible without actually reaching it. During storage, the ATP concentration characteristically remains level or even increases for a period of time early in storage and then declines. When the RBC ATP concentration falls below 2 µmol/g Hb, RBC recovery is typically below 75%. RBC's lose 2,3-DPG early in storage. The starting concentration is characteristically about 15 µmol/g Hb or about 1.1 mol/mol Hb. The concentration typically falls to one-tenth the starting amount in 7 to 10 days. The rate of synthesis of 2,3-DPG is a function of pH, occurring in excess above pH 7.2 but with breakdown favored below that pH. Attempts to increase 2,3-DPG syntheses by increasing storage-system pH have been limited by the mole for mole loss of ATP synthesis with each 2,3-DPG molecule formed. Thus, raising RBC 2,3-DPG concentrations, something previously considered to be desirable, actually tends to reduce RBC storage time.

A more acidic environment diminishes RBC metabolism. The pH of 7.2 is the point wherein a mechanism, known as the Rappaport shunt (see Hess et al. "Alkaline CPD and the preservation of red blood cell 2,3-DPG" (2002) Transfusion, 42:747-752, fully incorporated herein by reference) is triggered whereby 2,3-DPG is synthesized from 1,3-DPG, consuming the phosphate needed for the synthesis of ATP and, additionally, routing around a glycolytic step which produces two of the glycolytically generated ATPs. The net effect to the system is a depletion of ATP. If the intracellular pH can be maintained below 7.2, the shunt is effectively closed down and ATP synthesis is maximized. In a natural state, the shunt operates to some extent and the production and maintenance of some 2,3-DPG is important to other cellular events. However, the present inventors discovered that for purposes of preservation of the red blood cell during storage outside of the in vivo environment, minimization of the shunt operation is desirable.

Therefore, embodiments of the present inventive composition provide that the pH buffering system is present in an amount sufficient for the composition to be operable to maintain a pH of a red blood cell (RBC) suspension to which the composition is added at a value sufficient to establish and maintain during a storage period a reaction equilibrium in the red blood cell that favors glycolysis over synthesis of 2,3-diphosphoglycerate (DPG) from 1,3-DPG, thereby generating a net gain in adenosine tri phosphate (ATP) synthesis with respect to the reaction equilibrium during the storage period. A specific embodiment of the presently inventive compositions provides that the composition is operable to maintain the pH of the RBC suspension to which the composition has been added at between about 6.4 and 7.4. In more specific embodiments, the composition is operable to maintain the pH of the red blood cell (RBC) suspension to which the composition has been added at between 7.0 and less than about 7.2. In very specific embodiments the composition is operable to maintain the pH of the red blood cell (RBC) suspension to which the composition has been added at a value greater than about 7.1 and less than 7.2.

The present inventors have formulated additive solution compositions substantially free of chloride that surprisingly yields no negative effect on the system and permits the addition of increased amounts of the buffering system to provide additional pH buffering. One embodiment of the invention is directed to an aqueous composition for storage of red blood cells at about 1 to about 6° C. as well. This composition comprises: adenine; dextrose; at least one nonmetabolizable membrane-protectant sugar; and a pH buffering system. The pH buffering system comprises a combination of physiologically acceptable buffering agents including at least one agent providing bicarbonate anions, at least one agent providing phosphate anions, and at least one agent providing sodium cations. The pH buffering system is present in an amount sufficient for the composition to be operable to maintain a pH of a red blood cell (RBC) suspension to which the composition is added at a value sufficient to establish and maintain during a storage period a reaction equilibrium in the red blood cell that favors glycolysis over synthesis of 2,3-diphosphoglycerate (DPG) from 1,3-DPG, thereby generating a net gain in adenosine tri phosphate (ATP) with respect to the reaction equilibrium during the storage period. The composition is substantially free of exogenously derived chloride ions. As used herein, "substantially free of exogenously derived chloride ions" is defined as whatever the concentration of chloride ions is given that no source of chloride ions has been added to the composition.

Additional embodiments are directed to a suspension of red blood cells comprising any of the inventive compositions, and embodiments wherein the suspension is suitable for direct infusion into a patient in need of such an infusion.

Further embodiments of the inventive composition provide that the at least one agent providing sodium cations is selected from the group consisting of sodium bicarbonate, disodium phosphate, and combinations thereof. In a more specific embodiment the at least one agent providing bicarbonate anions is sodium bicarbonate. Additional embodiments provide that the at least one agent providing phosphate ions is selected from the group consisting of sodium phosphate, disodium phosphate, trisodium phosphate, and combinations thereof. In more specific embodiments the at least one agent providing phosphate ions is disodium phosphate. In other embodiments of the inventive composition the combination of physiologically acceptable buffering agents additionally comprises at least one agent providing a physiologically acceptable cation selected from the group consisting of $H^+$, potassium, ammonium, magnesium and combinations thereof.

In a further embodiment of the present inventive compositions, the at least one non-metabolizable membrane-protectant sugar is mannitol. Some sugar alcohols, in particular the monosaccharide-derived sugar alcohols (e.g., sorbitol, mannitol, xylitol, erythritol), are small hydrophilic molecules that appear to diffuse readily through some lipid barriers and may play an important role in cellular stability. Mannitol, in particular, is a known antioxidant that acts as a hydroxyl radical scavenger in vivo. It appears to play a substantial role in the maintenance of cell membrane integrity and is considered a membrane-protectant sugar. Other small polyols may also function as membrane protectant sugars. It is significant to note that glucose and mannitol have the same mole weight, that is, 180 g/mole. Sugar alcohols are not metabolized by the red blood cell.

As used herein, the reported osmolarity is an empirically derived value. Osmolarity is a measure of the osmotic pressure exerted by a solution across a perfect semi-permeable membrane (one which allows free passage of water and completely prevents movement of solute) compared to pure water. Osmolarity is dependent on the number of particles in solution but independent of the nature of the particles. The osmolarity of a simple solution is equal to the molarity times the number of particles per molecule. Real solutions may be much more complex. Proteins with many equivalents/L may only contribute a small amount to the osmolarity, since they consist of a few very large "particles". Not all ions are free in a solution. Cations may be bound to other anions or to proteins. Not all the solution volume is aqueous. To be truly accurate, all these factors should be included in the calculation.

Tonicity, a value highly related to osmolarity and somewhat more useful for describing biocellular conditions, is a measure of the osmotic pressure that a substance can exert across a cell membrane, compared to blood plasma. Osmolarity measures the effective gradient for water assuming that all the osmotic solute is completely impermeant. It is simply a count of the number of dissolved particles. A 300 mM solution of glucose and a 150 mM solution of NaCl each have the same osmolarity, for example. However, a cell placed in each of these solutions would behave very differently. Tonicity is a functional term describing the tendency of a solution to resist expansion of the intracellular volume.

Additional embodiments provide that the inventive compositions have an osmolarity of from about 200 to about 310 mOsm. In more specific embodiments the compositions have an osmolarity of from about 221 to about 280 mOsm. In a very specific embodiment the osmolarity is about 270 mOsm.

As noted, RBCs metabolize glucose (d-glucose="dextrose") to make ATP. The waste products are lactate and protons. The protons accumulate, driving down the pH and inhibiting further metabolism. Bicarbonate has been suggested as a buffer system wherein it combines with the protons and, in the presence of RBC carbonic anhydrase, is converted to water and carbon dioxide. In a storage container that permits diffusion of the carbon dioxide, the reverse reaction is prevented and the reaction is driven toward the formation of CO2. A buffering system based on bicarbonate has considerable capacity. Bicarbonate in physiologic concentrations in the additive solution creates the $pCO_2$ in the solution that drives the diffusion of up to 1 to 2 mmol of $CO_2$ from a 600 mL PVC bag each week. However, previous attempts to formulate RBC storage additive solutions with bicarbonate have failed with respect to increasing ATP synthesis and prolonging the effective storage period. For instance, Beutler (BAG-PM) described the addition of bicarbonate to RBC storage solutions, but failed to control for a high pH that led to rapid ATP depletion.

In discovering that saline is not a necessary ingredient to RBC additive solution compositions, and that the concentration of dextrose could be lowered without negative effects on ATP synthesis, the present inventors were able to utilize the resultant increased "play" in solution parameters to increase and fine-tune the pH buffering system. The presently disclosed buffering system provides not only an initially appropriate pH to the additive solution composition, but is able to impart to the RBC suspension a pH that, in turn, modulates the intracellular pH of the RBC to maximize ATP synthesis. The buffering system achieves these pH modulation targets over the storage period. Hence, the buffering capacity or strength of the pH buffering system is deliberately controlled. One embodiment of the present inventive compositions provide that the composition have a pH of from about 8 to about 9. In more specific embodiments the pH is from about 8.2 to about 8.8. In even more specific embodiments the pH of the composition is from about 8.4 to about 8.6, and in a very specific embodiment the pH of the composition is about 8.5. Another embodiment is directed to the inventive compositions wherein the buffering system has a buffering capacity in the red blood cell (RBC) suspension to which the composition is added which increases by at least about 2 mEq between a pH of 6.5 and 7.2 over a storage period of 6 weeks. The presently disclosed buffering system should provide a buffering capacity of at least this value, but is capable of providing even greater buffering capacities to the RBC suspension thereby lengthening the storage period even further.

The present inventors determined ranges for the necessary composition ingredients that permit the instantly disclosed advantages. In one embodiment of the inventive composition, the composition comprises adenine in an amount of about 1-3 mM, dextrose in an amount of from about 20 to about 115 mM, un-metabolizable membrane-protectant sugar in an amount of about 15 to about 60 mM, sodium bicarbonate in an amount from about 20 to about 130 mM, and disodium phosphate in an amount of from about 4 to about 20 mM. In a more specific embodiment the composition comprises adenine in an amount of about 2 mM, dextrose in an amount of from about 60 to about 100 mM, unmetabolizable membrane-protectant sugar in an amount of about 40 to about 60 mM, sodium bicarbonate in an amount of from about 22 to about 40 mM, and disodium phosphate in an amount of from about 7 to about 15 mM. In an even more specific embodiment the composition comprises adenine in an amount of about 2 mM, dextrose in an amount of about 80 mM, unmetabolizable membrane-protectant sugar in an amount of about 55 mM, sodium bicarbonate in an amount of about 26 mM, and disodium phosphate in an amount of about 12 mM, and the composition has a pH of about 8.5.

The present invention also provides method embodiments. In one such embodiment a method of preserving red blood cells (RBCs) for a storage period is provided. The method comprises: (a) mixing a sample of collected whole blood containing the RBCs to be stored and plasma with an anticoagulant solution, thereby forming a suspension of collected whole blood; (b) treating the suspension of collected whole blood to deplete the plasma and concentrate the RBCs, thereby forming packed RBCs; (c) mixing the packed RBCs with an amount of an aqueous composition sufficient to form a suspension of RBCs having about 35% to about 70% RBCs by volume; (d) cooling the suspension of RBCs to about 1 to about 6° C.; and (e) storing the cooled suspension of RBCs according to standard bank procedures known in the art. The aqueous composition consists essentially of: adenine; dextrose; at least one non-metabolizable membrane-protectant sugar; and a pH buffering system. The pH buffering system comprises a combination of physiologically acceptable buffering agents including at least one agent providing bicarbonate anions, at least one agent providing phosphate anions, and at least one agent providing sodium cations, wherein the pH buffering system is present in an amount sufficient for the composition to be operable to maintain a pH of a red blood cell (RBC) suspension to which the composition is added at a value sufficient to establish and maintain during a storage period a reaction equilibrium in the red blood cell that favors glycolysis over synthesis of 2,3-diphosphoglycerate (DPG) from 1,3-DPG, thereby generating a net gain in adenosine tri phosphate (ATP) synthesis with respect to the reaction equilibrium during the storage period. The solution is divided in manufacture to separate the dextrose and the phosphate and bicarbonate during heat sterilization.

RBCs useful in the present invention are those that have been separated from their plasma and resuspended in an anticoagulant solution in the normal course of component manufacture. Briefly stated, a standard whole blood sample (450.+/−45 ml) containing RBCs and plasma is mixed with an anticoagulation solution (about 63 ml) to form a suspension of whole blood. Proportional increases or decreases in solution volumes to reflect different donor blood volumes such as 400.+/−40 ml-500.+/−50 ml can also be used. The whole blood suspension is thereafter centrifuged to separate the RBCs from the blood plasma thereby forming packed RBCs. The performance of the overall process is improved by leukocyte reduction using conventional techniques.

Suitable anticoagulants include conventional anticoagulants known for storage of RBCs. Preferably; the anticoagulants include citrate anticoagulants having a pH of 5.5 to 8.0, e.g. CPD, half-strength CPD and the like. The most preferred anticoagulant is CPD.

The RBC suspension is then generally stored in standard polyvinyl chloride (PVC) blood storage bags using either the collection bag or PVC transfer packs of different sizes depending on the volume of the stored aliquot. The RBC suspension is stored at about 1 to 6° C. according to standard blood bank procedure as described in Clinical-Practice of Blood Transfusion editors: Petz & Swisher, Churchill-Livingston publishers, N.Y., 1981. All documents cited herein infra and supra are hereby incorporated by reference thereto. In a specific embodiment of the inventive method, the suspension of RBCs is suitable for direct infusion into a patient in need of such an infusion. While PVC blood storage bags are the industry-approved standard; the present invention contemplates storage in a wide variety of bags adapted for RBC suspension storage, for example, by including appropriate plastisizers as needed. Ingredients related to the bag or container component of RBC storage technology are not discussed herein but it will be readily apparent to one of ordinary skill in the art that many container technologies may be employed to practice the present invention.

The additive solutions of the invention can also be used to rehydrate lyophilized RBC or in the thawing of stored frozen blood or blood component, e.g. RBC.

In specific embodiments of the inventive method of preserving RBCs, the at least one non-metabolizable membrane-protectant sugar is a monosaccharide derived sugar alchohol and in a more specific embodiment the non-metabolizable membrane-protectant sugar is mannitol. In additional embodiments of the method, the at least one agent providing sodium cations is selected from the group consisting of sodium bicarbonate, disodium phosphate, and combinations thereof. In specific embodiments the at least one agent providing bicarbonate anions is sodium bicarbonate. Further embodiments are directed to the inventive method of preserving RBCs wherein the at least one agent providing phosphate ions is selected from the group consisting of sodium phosphate, disodium phosphate, trisodium phosphate, and combinations thereof, and in more specific embodiments that at least one agent providing phosphate ions is disodium phosphate. In other embodiments of the inventive method the combination of physiologically acceptable buffering agents additionally comprises at least one agent providing a physiologically acceptable cation selected from the group consisting of $H^+$, potassium, ammonium, magnesium and combinations thereof.

Further embodiments are directed to the inventive method of preserving RBCs wherein the composition has an osmolarity of from about 200 to about 310 mOsm. In specific embodiments the osmolarity is from about 221 to about 280 mOsm, and in a very specific embodiment the osmolarity is about 270 mOsm. In other embodiments inventive methods are provided wherein the composition has a pH of from about 8 to about 9. In specific embodiments the pH is from about 8.2 to about 8.8 and in more specific embodiments the pH of the composition is from about 8.4 to about 8.6. In a very specific embodiment the pH of the composition is about 8.5. An additional embodiment of the inventive method of preserving RBCs provides that the buffering system has a buffering capacity in the red blood cell (RBC) suspension to which the composition is added which increases by 2 mEq between a pH of 6.5 and 7.2 over a storage period of 6 weeks.

The present invention also provides embodiments of the inventive method of preserving RBCs wherein the composition is operable to maintain the pH of the red blood cell (RBC) suspension to which the composition has been added at between about 6.4 and about 7.4. In specific method embodiments the composition is operable to maintain the pH of the red blood cell (RBC) suspension to which the composition has been added at between 7.0 and less than about 7.2, and in even more specific method embodiments the composition is operable to maintain the pH of the red blood cell (RBC) suspension to which the composition has been added at a value greater than about 7.1 and less than 7.2.

Methods according to the present invention directed to specific ranges of the necessary ingredients of the composition are also provided. In one method embodiment the composition comprises adenine in an amount of about 1-3 mM, dextrose in an amount of from about 20 to about 115 mM, un-metabolizable membrane-protectant sugar in an amount of about 15 to about 60 mM, sodium bicarbonate in an amount from about 20 to about 130 mM, and disodium phosphate in an amount of from about 4 to about 20 mM. In a more specific embodiment the composition comprises adenine in an amount of about 2 mM, dextrose in an amount of from about 60 to about 100 mM, unmetabolizable membrane-protectant sugar in an amount of about 40 to about 60 mM, sodium bicarbonate in an amount of from about 22 to about 40 mM, and disodium phosphate in an amount of from about 7 to about 15 mM, and in a very specific embodiment the composition comprises adenine in an amount of about 2 mM, dextrose in an amount of about 80 mM, unmetabolizable membrane-protectant sugar in an amount of about 55 mM, sodium bicarbonate in an amount of about 26 mM, and disodium phosphate in an amount of about 12 mM, and further wherein the composition has a pH of about 8.5.

In accordance with the method of the invention, additive solution is added to the packed RBC suspension in an amount sufficient to provide a therapeutically effective amount of recoverable RBCs in the cell suspension. Preferably, the additive solution is added at a volume ranging from about 60 ml to about 400 ml, preferably about 100 to about 150 ml, most preferably about 110 ml. The solution is typically used in a 1:4.5 volume ratio of solution to whole blood collected (100 mL for a 450 mL whole blood collection, 111 mL for a 500 mL whole blood collection, or equivalent). In specific embodiments of the present inventive methods of preserving RBCs, the volume ratio of the composition to the collected whole blood is about 1:4.5. In a more specific embodiment the volume of the composition is about 110 mL and the volume of the collected whole blood is about 500 mL.

The RBC volume fraction in the cell suspension, i.e. after addition of additive solution, is about 27 to 70% of the total suspension. More preferably, the RBC volume fraction in the cell suspension is about 35 to about 50%. Most preferably, the RBC volume fraction in the cell suspension is about 43% of the total suspension.

Over the course of the storage period the present inventors monitored and collected data relevant to the health of the red blood cell. As noted in FIGS. 1 and 2, storage according to the present invention resulted in superior red blood cell quality for longer durations as smaller volumes. As noted above, the blood storage "lesion" is an apoptotic event and the red blood cell membrane undergoes physiological and morphological changes commensurate with programmed cell death. Over the course of the storage period, it is known that the red blood cell membrane surface area decreases so that its shape changes from the biconcave shape that permits maximum surface area per volume, facilitating diffusion of gases and nutrients, to a more spherical shape characteristic of a dying, fragile cell. The red blood cell membrane is initially flexible and deformable, facilitating passage through small capillaries. This overall shape change is accompanied by the pinching off from the membrane of microvesicles, forming spicules on the outer surface of the red blood cell, so that a cell at the end stage this process, upon observation, resembles a spiny urchin (hence the process is referred to as an echinocytic change and the final form prior to lyses is called an echinocyte). The ensuing fragility eventually leads to lyses and death of the cell. Determining hemolysis rate permits an indication of the scope and severity of this activity. In addition to engendering unacceptable levels of hemolysis during storage, these morphological changes trigger clearance mechanisms within a recipient patient's body upon re-infusion of the stored red blood cells, decreasing the post-infusion recovery and decreasing the efficiency of the transfusion. Employment of the compositions according to the present invention, and methods of preserving red blood cells which utilize them, leads to a decreased osmotic fragility, and a decreased rate of hemolysis. This corresponds to in increase in retention of cell membrane surface area and morphological state, and, therefore, an increase in recovery of viable red blood cells and a decrease in post-infusion clearance of the re-infused red blood cells from the recipient patient's body.

One embodiment of the present invention provides a method of improving red blood cell (RBC) membrane maintenance and suppressing RBC apoptosis during a storage period. The method comprises storing the RBCs during the storage period in suspensions to which the inventive compositions have been added. In a specific embodiment, the microvesicular concentration is reduced about 75% from concentrations observed in red blood cells stored for the same storage period in RBC suspensions comprising AS-3.

Another embodiment of the present invention provides a method of decreasing red blood cell (RBC) fragility and suppressing RBC hemolysis during a storage period. The method comprises storing the RBCs during the storage period in suspensions to which the inventive compositions have been added. A further embodiment is directed to methods of increasing viability of red blood cells (RBCs) subsequent to a storage period and after infusion into a patient in need of such an infusion, and decreasing a rate of post-infusion clearance of the RBCs by the patient. The methods comprise storing the RBCs during the storage period in suspensions to which the inventive compositions have been added.

The inventive additive solution composition confers several advantages over prior art additive solutions. The red blood cells stored therein may be stored longer, at least 8 weeks with better radioactive chrome-labeled RBC 24 hour in vivo recovery, than any presently licensed solution. Use of the inventive compositions clearly diminishes the scope and severity of the storage lesion. During the storage period, the red blood cells exhibit an acceptable range of hemolysis: 0.2% at 6 weeks and 0.4% at 8 weeks, all below the FDA limit of 1% at the end of licensed storage. Red blood cells stored in the inventive additive solutions exhibit less membrane loss during storage as demonstrated by lower concentrations of membrane microvesicles and less osmotic fragility. Preservation of membrane during storage is expected to help RBC stored in solution to have better flow properties than cells that have lost more membrane. Retention of normal membrane physiology also suppresses the mechanisms present in the recipient-patient's body that trigger selective clearance from circulation and destruction of red blood cells. Hence, the re-infused red blood cells last longer in the recipient-patient and enhanced longer-term recovery of the re-infused red blood cells is possible. Moreover, enhanced longer-term survival of infused red blood cells should lessen the need for repeat transfusions lowering associated risks to the patient. The inventive solutions also permit higher RBC ATP concentrations during the late phases of storage, which is expected to allow better RBC ATP secretion and therefore improved flow and longevity after the cells are transfused. Pragmatically, the present solutions are useful while working with conventional collection systems that collect whole blood in CPD or CP2D for the production of fresh frozen plasma and random donor platelets, or for the collection of fresh whole blood in emergencies.

The following examples are provided for illustrative purposes only and should not be construed as limiting the scope of the present invention as defined herein by the claims.

EXAMPLES

TABLE 1

Compositions of the Tested Additive Solutions (concentrations in mM)

|  | AS-3 | EAS-61 | EAS-78 | EAS-81 |
|---|---|---|---|---|
| NaCl | 70 | 26 | 30 |  |
| NaHCO$_3$ |  |  | 30 | 26 |
| NaH$_2$PO$_4$ | 23 |  |  |  |
| Na$_2$HPO$_4$ |  | 12 | 9 | 12 |
| Adenine | 2 | 2 | 2 | 2 |
| Na$_3$Citrate | 18 |  |  |  |
| Dextrose | 55 | 110 | 50 | 80 |
| Mannitol |  | 55 | 30 | 55 |
| Volume | 110 | 170 | 170 | 110 |
| pH | 5.8 | 8.3 | 8.4 | 8.5 |

Example 1

This example illustrates a performance profile and the advantages of one embodiment of the inventive additive solution composition, designated as EAS-81 (see Table 1). EAS-81 and comparative example AS-3 (Nutricel, Pal Biomedical) are both provided in conventional volumes, while comparative examples EAS-61 and EAS-78 are provided in more dilute, larger volumes. EAS-81 and EAS-78 both comprise bicarbonate. See FIG. 1, wherein the bicarbonate-containing compositions are represented by circles, while those without bicarbonate are represented by diamonds. Higher volume compositions are represented by solid figures while the conventional volume compositions are represented by open figures. All volumes of additive solution compositions disclosed herein are understood to be per 500 mL unit of whole blood for an approximate volumetric ratio of 1:4.5.

The first example is conducted as a pooling study in order to evaluate the effect of storage solution ingredients on RBC metabolism and integrity over the course of 10 weeks of storage in PVC bags. Pooling reduces the largest source of variability in conventional blood storage studies, that is, the innate differences between the RBCs from different donors. Pooling places some of the cells from each donor in every group of the study while maintaining conventional unit size.

RBC units, unreactive in the indirect antiglobulin test (IAT) are grouped into sets of 4 ABO-identical units. Each set is then pooled, mixed and aliquoted to make four identical pooled units. One unit from each pool is used in each of the four arms of the study.

The compositions of AS-3 and the EASs are disclosed in Table 1. The EASs are made in the laboratory from USP adenine, sugars and salts available from Sigma Chemicals, St. Louis, Mo., and sterilely filtered into one-liter storage bags (Code 4R2032, Baxter Healthcare, Deerfield, Ill.), as detailed in Hess et al. "The effects of phosphate, pH, and AS volume on RBCs stored in saline-adenine-glucose-mannitol solutions," *Transfusion*, vol. 40: 1000-1006, August 2000, fully incorporated herein by reference. The storage bags are held at 37° C. for two weeks. The solutions are then cultured and the cultures incubated for another two weeks. Sterility is confirmed by the absence of bacterial and fungal growth for 7-14 days (SeptiCheck, Becton-Dickinson Microbiology Systems, Sparks, Md.), and the solutions are aliquoted by weight into 600 mL PVC bags (Code 4R2023, Baxter Healthcare Corp., Deerfield, Ill.). All connections are made using a sterile connecting device (SCD 312, Terumo Medical Corp. Elkton, Md.).

RBC Unit Preparation:

Standard units of blood (500±55 mL) are collected in 70 mL of CP2D solution in a triple-bag collection system (Item code #127-23, Pall Corporation, East Hills, N.Y.). Units are leukoreduced with the integral leukoreduction filter. Packed RBCs are prepared by centrifugation for 5 minutes followed by removal of all but 65 mL of the plasma, after which the listed volume of AS or EAS is added sterilely. Units are stored upright at 1-6° C. for 10 weeks except for approximately weekly mixing and removal of a 15 mL sample.

In Vitro Measurements

Leukoreduction (elimination of white blood cells from the whole blood product) is confirmed by flow cytometry. The total hemoglobin (Hb) concentration is measure with a clinical hematology analyzer (Hematology Cell Counter System Series 9110+, Baker, Allentown, Pa.). Mean cell volume (MCV is determined from the RBC count and the microhematocrit of the storage suspension. Supernatant Hb is measured spectrophotometrically using the modified Drabkin assay as discussed in Moore et al., "A micromodification of the Drabkin hemoglobin assay for measuring plasma hemoglobin in the range of 5 to 2000 mg/dl. *Biochem Med* 26:167-173 (1981), incorporated fully herein by reference. Percent hemolysis is determined by measuring the ratio of free to total Hb and the hematocrit.

RBC ATP concentrations are measured in supernatants of deproteinized PRBCs. Cell aliquots are mixed with cold 10% trichloroacetic acid to precipitate blood proteins, centrifuged at 2700×g for 10 minutes, and the protein free supernatant frozen at −80° C. until tested. ATP is assayed enzymatically using a commercially available test kit (Procedures 366-UV, Sigma Diagnostics, St. Louis, Mo.).

Blood gases, bicarbonate, and pH are measured or calculated on a blood gas analyzer (Corning 855, Ithica, N.Y.). Thus, pH is measured at 37° C. Extracellular sodium, potassium, chloride, phosphate, lactate, and glucose are measured on a programmable chemical analyzer (Hitachi 902 Analyzer, Boehringer Mannheim Corporation, Indianapolis, Ind.). The average degree of RBC shape change from discocytes to echinocytes to spherocytes is measured according to the method of Usry, Moore, and Manolo, described in "Morphology of stored, rejuvenated human erythrocytes" *Vox Sang* 28:176-183 (1975), fully incorporated herein by reference. Microvesicles are measured in the supernatant at the end of storage. Plasma is untracentrifuged, the vesicle pellet washed three times in saline, and then the total protein is quantified using Bradford's method (BioRad, Richmond, Calif.).

Figure 2:
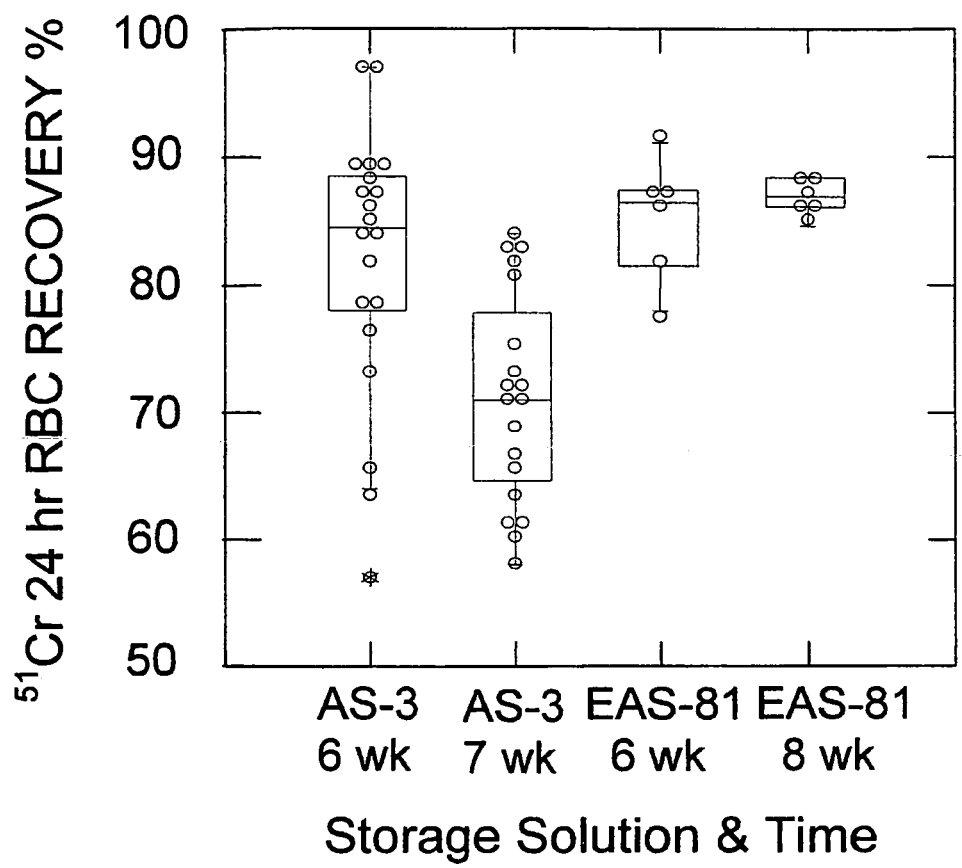
FIG. 2: illustrates the in vivo recovery of red blood cells sampled 24 hours after re-infusion into a subject for RBCs stored in EAS-81 for 6 weeks (n=6), EAS-81 for 8 weeks (n=6), compared to a historic control, the licensure study for AS-3 published by Simon et al. in 1985. Both studies used the $^{51}Cr$ single-label method.

The results of the comparison testing of the 4 RBC storage solutions are illustrated in FIGS. 1 and 2. In all storage solutions, RBC ATP concentrations increased in the first week of storage (FIG. 1A). In the EASs the ATP concentration continued to rise in the second week and remained higher than in the AS-3 for the duration of the study. At eight weeks of storage and beyond, EAS-81 exhibited ATP concentrations equivalent to the increased-volume EAS-61, while EAS-78, having both the increased volume and bicarbonate buffer system, exhibited somewhat higher concentrations.

Hemolysis (the breakdown of red blood cells), increases with duration of storage in all storage solutions (FIG. 1$b$). At all times, however, hemolysis was higher in AS-3. It was modestly reduced in EAS-81 and reduced further in the other EASs. There was no additional reduction of hemolysis with bicarbonate in the high volume solutions. As expected, a lower AS volume resulted in a higher storage hematocrit (FIG. 1$c$) and RBCs lost volume in all of the solutions during storage.

Lactate concentrations were higher across all time points in the bicarbonate-containing EASs (FIG. 1$d$). Total lactate production over 8 weeks of storage was 9 mM in AS-3, 12 mM in EAS-61, 13 mM in EAS-81, and 15 mM in EAS-78. Extra and intracellular pH was also higher at most time points, but the differences in intracellular pH did not achieve statistical significance (FIGS. 1$e$ and 1$f$). The time course of bicarbonate loss and PCO2 rise and fall that provide the buffering in the suspending solution is shown in FIGS. 1$g$ and 1$h$.

Generally, comparison of the inventive EAS-81 to the AS-3 stored cells reveals greater energy utilization with resultant higher ATP concentrations, less hemolysis better morphology, less microvesiculation, and slightly higher pH in the former. The older EAS's, especially EAS-78, perform even better in certain respects, but their greater volume results in greater dilution of the stored RBC which could result in hemodilution of multiply-transfused patient recipients.

Example 2

This example illustrates that an inventive EAS formulation permitted the storage of RBC in conventional-volume additive solution for 8 weeks, with better recovery, lower hemolysis and enhanced membrane preservation over the known 6-week storage solution.

12 volunteer subjects meeting the United States Food and Drug Administration (FDA) and American Association of Blood Banks donor criteria were selected. The subjects donated 500 mL (one unite) of whole blood, which was collected in CP2D primary bag (Item code #127-23, Pall Corporation, East Hills, N.Y.), and leuko-reduced with all but about 65 mL of the plasma removed. EAS-81, 110 mL, was added and the packed RBC solutions were stored upright at 1-6° C. with half the samples (n=6) being stored for 6 weeks and half (n=6) for 8 weeks. The week prior to the end of storage, the units were sterilely sampled and cultured. If the culture exhibited no growth, a small aliquot of the stored RBC was labeled with 51-Cr and returned to the donor using the Moroff protocol for single label measurement of RBC recovery.

Graphs of means and standard errors were created and other descriptive statistics of the storage groups were calculated using spreadsheet program software (Excel, Microsoft, Redmond, Wash.). Lactate production in each of the storage systems was calculated from the beginning and ending concentrations and the storage system volumes were adjusted to account for the hemoglobin and serum protein content. Box plots of RBC recovery values were produced using SyStat Ver. 6 (SPSS Inc., Chicago, Ill.).

Leuko-reduced RBC stored in CP2D/EAS-81 for 6 weeks had an average autologous 24-hour in vivo recovery of 85±5%, with in vivo recovery after 8 weeks at 87±2% (FIG. 2). The apparent anomaly of higher recovery at longer time is probably a result of the small size of the study and the great variability in the storability of blood form different individuals. These recoveries, however, are superior to any currently licensed storage solution and would meet the criteria for licensure in the US and Europe (that is, exhibiting a recovery greater than 75% and hemolysis less than 1% for the U.S., or a recovery greater than 75% and hemolysis less than 0.8% for Europe). RBC Hemolysis fraction during this study was 0.2±0.2 at six weeks and 0.4±0.2 at 8 weeks. RBC microvesicle protein concentrations were 8±4 at 6 weeks and 12±6 mg/dL RBC at 8 weeks, and thus accounted for only about 5% of the RBC hemoglobin loss.

The superior storage performance of the inventive EAS-81 in terms of both duration of storage and improved physiological functioning of the infused product, appears to derive from several bases. First, the novel pH modulating system permits sustained buffering of the pH of the suspended solution across the tested storage period which is sufficient to maintain a pH in the intracellular space sufficient to drive the internal cell equilibrium toward glycolysis and away from the ATP-consuming production of 2,3-DPG. In addition, the higher extracellular phosphate concentrations in this formulation contribute toward limiting extracellar Ca++ concentrations, which in turn suppresses several apoptotic processes such as phospholipids scrambling and membrane deformation and loss. This leads to improved post-infusion recovery and a higher membrane quality in the infused RBCs, further diminishing the triggering of rapid in vivo clearance mechanisms in infused patients and resulting a higher percentage of recoverable infused RBCs for an extended period beyond infusion. The EAS-81 formulation, which eliminates NaCl in favor of increasing the amount of the particular buffering compounds while maintaining suitable osmolarity, permits more effective, longer lasting pH modulation of the RBC-additive solution suspension, and more phosphate available to minimize adverse cellular events associated with increasing Ca++ concentrations and decreasing ATP concentration. Moreover, the ability to formulate EAS-81 in conventional volumes makes it particularly suitable for use in multiply and massively transfused patients.

What is claimed is:

1. An aqueous composition, in a volume ratio of 1:4.5 of solution to whole blood collected, for storage of red blood cells at about 1 to about 6° C., the composition free of exogenously derived chloride ions and consisting of:
   adenine;
   dextrose in an amount of from about 60 to about 100 mM;
   at least one non-metabolizable membrane-protectant sugar; and
   a pH buffering system,
wherein the pH buffering system consists of sodium bicarbonate in an amount of about 26 mM, and disodium phosphate, wherein the pH buffering system is present in an amount sufficient for the composition to be operable to maintain a pH of a red blood cell suspension to which the composition is added at a value sufficient to establish and maintain during a storage period a reaction equilibrium in the red blood cells that favors glycolysis over synthesis of 2,3-diphosphoglycerate (DPG) from 1,3-DPG, thereby generating a net gain in adenosine tri phosphate (ATP) synthesis with respect to the reaction equilibrium during the storage period.

2. The composition as recited in claim 1, wherein the at least one non-metabolizable membrane-protectant sugar is mannitol.

3. The composition as recited in claim 1 having an osmolarity of from about 200 to about 310 mOsm.

4. The composition as recited in claim 3 wherein the osmolarity is from about 221 to about 280 mOsm.

5. The composition as recited in claim 4, wherein the osmolarity is about 270 mOsm.

6. The composition as recited in claim 1 having a pH of from about 8 to about 9.

7. The composition as recited in claim 6, wherein the pH is from about 8.2 to about 8.8.

8. The composition as recited in claim 7, wherein the pH of the composition is from about 8.4 to about 8.6.

9. The composition as recited in claim 8, wherein the pH of the composition is about 8.5.

10. The composition as recited in claim 1, wherein the buffering system has a buffering capacity in the red blood cell (RBC) suspension to which the composition is added which increases by at least about 2 mEq between a pH of 6.5 and 7.2 over a storage period of 6 weeks.

11. The composition as recited in claim 1, wherein the composition is operable to maintain the pH of the red blood cell (RBC) suspension to which the composition has been added at between about 6.4 and about 7.4.

12. The composition as recited in claim 1, wherein the composition is operable to maintain the pH of the red blood cell (RBC) suspension to which the composition has been added at between 7.0 and less than about 7.2.

13. The composition as recited in claim 1, wherein the composition is operable to maintain the pH of the red blood cell (RBC) suspension to which the composition has been added at a value greater than about 7.1 and less than 7.2.

14. The composition as recited in claim 1, comprising adenine in an amount of about 1-3 mM, at least one non-metabolizable membrane-protectant sugar in an amount of about 15 to about 60 mM, and disodium phosphate in an amount of from about 4 to about 20 mM.

15. The composition as recited in claim 14, comprising adenine in an amount of about 2 mM, at least one non-metabolizable membrane-protectant sugar in an amount of about 40 to about 60 mM, and disodium phosphate in an amount of from about 7 to about 15 mM.

16. The composition as recited in claim 15, comprising adenine in an amount of about 2 mM, dextrose in an amount of about 80 mM, at least one non-metabolizable membrane-protectant sugar in an amount of about 55 mM, and disodium phosphate in an amount of about 12 mM, and further wherein the composition has a pH of about 8.5.

17. The composition according to claim 1 in which the length of storage for the red blood cells is for an at least 8 week period.

18. A suspension of red blood cells consisting of red blood cells and the composition as recited in claim 1.

19. The suspension as recited in claim 18, wherein the suspension is suitable for direct infusion into a patient in need of such an infusion.

20. A suspension of red blood cells consisting of red blood cells and the aqueous composition of claim 1, wherein the red blood cell volume fraction is about 27 to about 70% of the total suspension.

21. An aqueous composition, in a volume ratio of 1:4.5 of solution to whole blood collected, for storage of red blood cells for an at least 8 week period at about 1 to about 6° C., the composition free of exogenously derived chloride ions and consisting of:
about 2 mM adenine;
about 80 mM dextrose;
about 55 mM of at least one non-metabolizable membrane-protectant sugar; and
a pH buffering system,
wherein the pH buffering system consists of sodium bicarbonate to provide bicarbonate anions at a concentration of about 26 mM, and disodium phosphate to provide phosphate anions at a concentration of about 12 mM, wherein the pH buffering system is present in an amount sufficient for the composition to maintain a pH of a red blood cell (RBC) suspension to which the composition is added at a value which is sufficient to establish and maintain during a storage period a reaction equilibrium in the red blood cell that favors glycolysis over synthesis of 2,3-diphosphoglycerate (DPG) from 1,3-DPG, thereby generating a net gain in adenosine tri phosphate (ATP) synthesis with respect to the reaction equilibrium during the storage period.

22. A suspension of red blood cells consisting of red blood cells and the aqueous composition of claim 21, wherein the red blood cell volume fraction is about 27 to about 70% of the total suspension.

23. An aqueous composition for storage of red blood cells at about 1 to about 6° C., the composition free of exogenously derived chloride ions and consisting of:
adenine;
dextrose in an amount of from about 60 to about 100 mM;
at least one non-metabolizable membrane-protectant sugar; and
a pH buffering system,
wherein the pH buffering system consists of sodium bicarbonate in an amount of about 26 mM, and disodium phosphate, wherein the pH buffering system is present in an amount sufficient for the composition to be operable to maintain a pH of a red blood cell (RBC) suspension to which the composition is added between about 6.4 and 7.4 during a storage period of ten weeks.

24. The composition as recited in claim 23, comprising adenine in an amount of about 1-3 mM, the at least one non-metabolizable membrane-protectant sugar in an amount of about 15 to about 60 mM, and disodium phosphate in an amount of from about 4 to about 20 mM.

25. The composition as recited in claim 24, comprising adenine in an amount of about 2 mM, the at least one non-metabolizable membrane-protectant sugar in an amount of about 40 to about 60 mM, and disodium phosphate in an amount of from about 7 to about 15 mM.

26. The composition as recited in claim 25, comprising adenine in an amount of about 2 mM, dextrose in an amount of about 80 mM, the at least one non-metabolizable membrane-protectant sugar in an amount of about 55 mM, and disodium phosphate in an amount of about 12 mM, and further wherein the composition has a pH of about 8.5.

27. A suspension of red blood cells consisting of the composition as recited in claim 23 at volumes of up to 150 mL and a volume of packed red blood cells, derived from the whole blood collected at volumes of up to about 555 mL.

28. A suspension of red blood cells consisting of red blood cells and the aqueous composition of claim 23, wherein the red blood cell volume fraction is about 27 to about 70% of the total suspension.

29. A suspension of red blood cells consisting of the composition as recited in claim 23 at a volume of about 110 mL and a volume of packed red blood cells, derived from the whole blood collected at a volume of about 500 mL.

30. An aqueous composition, in a volume ratio of about 1:4.5 of solution to whole blood collected, for storage of red blood cells at about 1 to about 6° C., the composition free of exogenously derived chloride ions and consisting of:
adenine;
dextrose in an amount of from about 60 to about 100 mM;
at least one non-metabolizable membrane-protectant sugar;
and a pH buffering system,
wherein the pH buffering system consists of sodium bicarbonate in an amount of about 26 mM, and disodium phosphate, wherein the pH buffering system is present in an amount sufficient for the composition to be operable to maintain a pH of a red blood cell (RBC) suspension to which the composition is added between about 6.4 and 7.4 during a storage period of ten weeks.

31. The composition as recited in claim 30, comprising adenine in an amount of about 1-3 mM, the at least one non-metabolizable membrane-protectant sugar in an amount of about 15 to about 60 mM, and disodium phosphate in an amount of from about 4 to about 20 mM.

32. The composition as recited in claim 31, comprising adenine in an amount of about 2 mM, the at least one non-metabolizable membrane-protectant sugar in an amount of about 40 to about 60 mM, and disodium phosphate in an amount of from about 7 to about 15 mM.

33. The composition as recited in claim 32, comprising adenine in an amount of about 2 mM, dextrose in an amount of about 80 mM, the at least one non-metabolizable membrane-protectant sugar in an amount of about 55 mM, and disodium phosphate in an amount of about 12 mM, and further wherein the composition has a pH of about 8.5.

34. A suspension of red blood cells consisting of red blood cells and the aqueous composition of claim 30, wherein the red blood cell volume fraction is about 27 to about 70% of the total suspension.

35. A suspension of red blood cells consisting of the composition as recited in claim 30 at a volume of about 110 mL and a volume of packed red blood cells, derived from the whole blood collected at a volume of about 500 mL.

36. An aqueous composition for storage of red blood cells for an at least 8 week period at about 1 to about 6° C., the composition free of exogenously derived chloride ions and consisting of:
about 2 mM adenine;
about 80 mM dextrose;
about 55 mM of at least one non-metabolizable membrane-protectant monosaccharide-derived sugar alcohol selected from the group consisting of sorbitol, mannitol, xylitol, erythritol; and
a pH buffering system,
wherein the pH buffering system consists of sodium bicarbonate to provide bicarbonate anions at a concentration of about 26 mM, disodium phosphate to provide phosphate anions at a concentration of about 12 mM, wherein the pH buffering system is present in an amount sufficient for the composition to maintain a pH of a red blood cell (RBC) suspension to which the composition is added between about 6.4 and 7.4 during a storage period of ten weeks.

37. A suspension of red blood cells consisting of the composition as recited in claim 36 at volumes of up to 150 mL and a volume of packed red blood cells, derived from the whole blood collected at volumes of up to about 555 mL.

38. A suspension of red blood cells consisting of red blood cells and the aqueous composition of claim 36, wherein the red blood cell volume fraction is about 27 to about 70% of the total suspension.

39. A suspension of red blood cells consisting of the composition as recited in claim 36 at a volume of about 110 mL and a volume of packed red blood cells, derived from the whole blood collected at a volume of about 500 mL.

* * * * *